United States Patent
Cui

(10) Patent No.: US 8,716,677 B2
(45) Date of Patent: May 6, 2014

(54) WAVEFRONT CORRECTION OF LIGHT BEAM

(75) Inventor: Meng Cui, Ashburn, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 291 days.

(21) Appl. No.: 13/353,029

(22) Filed: Jan. 18, 2012

(65) Prior Publication Data

US 2013/0015367 A1 Jan. 17, 2013

Related U.S. Application Data

(60) Provisional application No. 61/434,204, filed on Jan. 19, 2011.

(51) Int. Cl.
| | |
|---|---|
| *G01J 1/58* | (2006.01) |
| *G01B 9/02* | (2006.01) |
| *G02B 27/00* | (2006.01) |
| *A61B 5/00* | (2006.01) |
| *G01J 3/45* | (2006.01) |

(52) U.S. Cl.
CPC ........ *G01B 9/02091* (2013.01); *G02B 27/0031* (2013.01); *A61B 5/0062* (2013.01); *G01J 3/45* (2013.01)
USPC .................................... 250/459.1; 250/458.1

(58) Field of Classification Search
CPC ........... G01B 9/02091; G02B 27/0031; A61B 5/0062; G01J 3/45
USPC ........................................ 250/459.1, 458.1
See application file for complete search history.

(56) References Cited

U.S. PATENT DOCUMENTS

| | | | |
|---|---|---|---|
| 3,979,585 A | 9/1976 | O'Meara | |
| 5,120,128 A | 6/1992 | Ulich et al. | |
| 5,398,130 A | 3/1995 | Redman | |
| 5,684,545 A | 11/1997 | Dou et al. | |
| 6,486,943 B1 | 11/2002 | Burns et al. | |
| 6,556,854 B1 * | 4/2003 | Sato et al. | 600/407 |
| 6,771,417 B1 | 8/2004 | Wolleschensky et al. | |
| 7,274,442 B2 | 9/2007 | Dolne et al. | |
| 7,554,672 B2 | 6/2009 | Greenaway et al. | |
| 2001/0030740 A1 * | 10/2001 | Mori et al. | 355/53 |

(Continued)

OTHER PUBLICATIONS

Extended European Search Report in counterpart EP App. No. 12151624.9-2217; issued May 18, 2012, 6 pages.

(Continued)

*Primary Examiner* — David Porta
*Assistant Examiner* — Abra Fein
(74) *Attorney, Agent, or Firm* — DiBerardino McGovern IP Group LLC

(57) ABSTRACT

An apparatus includes a transverse scanning optical system in the path of a first light beam traveling along a first optic axis; a wavefront correction system in the path of a second light beam traveling along a second optic axis, the wavefront correction system including a wavefront correction device having a spatial phase profile on its surface; a beam combiner that receives the first light beam and the second light beam and outputs an interference beam having a beat frequency equal to a difference frequency between the first light beam and second light beam; and a detection system placed relative to a random scattering medium, which is in the path of the interference beam. The detection system detects measurement light produced by the random scattering medium while the interference beam strikes the random scattering medium.

20 Claims, 12 Drawing Sheets

(56) References Cited

U.S. PATENT DOCUMENTS

| | | | |
|---|---|---|---|
| 2002/0109078 A1* | 8/2002 | Housh et al. | 250/222.1 |
| 2003/0062464 A1* | 4/2003 | Byren et al. | 250/201.9 |
| 2004/0189999 A1* | 9/2004 | De Groot et al. | 356/497 |
| 2005/0187722 A1* | 8/2005 | Bechhoefer | 702/56 |

OTHER PUBLICATIONS

Biru Wang and Martin J. Booth, "Optimum deformable mirror modes for sensorless adaptive optics," Optics Communications 282 (2009) pp. 4467-4474.

Na Ji, et al., "Advances in the speed and resolution of light microscopy," Current Opinion in Neurobiology 2008, 18:605-616.

Gaddum Duemani Reddy and Peter Saggau, "Fast three-dimensional laser scanning scheme using acouto-optic deflectors," Journal of Biomedical Optics 10(6), 064038 (Nov./Dec. 2005), pp. 1-10.

Meng Cui and Changhuei Yang, "Implementation of a digital optical phase conjugation system and its application to study the robustness of turbidity suppression by phase conjugation," Optics Express, Feb. 15, 2010, vol. 18, No. 4, pp. 3444-3455.

James E. Harvey & Gary M. Callahan, "Wavefront error compensation capabilities of multi-actuator deformable mirrors," SPIE vol. 141, Adaptive Optical Components (1978), pp. 50-57.

James E. Pearson, "Atmospheric turbulence compensation using coherent optical adaptive techniques," Appl. Opt. 15, 622-631 (1976).

Rensheng Dou and Michael K. Giles, "Closed-loop adaptive-optics system with a liquid-crystal television as a phase retarder," Opt. Lett. vol. 20, No. 14; 1583-1585 (Jul. 15, 1995).

Richard W. Bowman, et al. "An SLM-based Shack-Hartmann wavefront sensor for aberration correction in optical tweezers." Journal of Optics 12 (2010) 124004 6 pp.

Tomas Cizmar, et al. "In situ wavefront correction and its application to micromanipulation." Nature Photonics vol. 4: 388-394 (Jun. 2010).

Meng Cui and Changhuei Yang, "Implementation of a digital optical phase conjugation system and its application to study the robustness of turbidity suppression by phase conjugation." Optics Express vol. 18, No. 4: 3444-3455 (Feb. 15, 2010).

Ivo M. Vellekoop and Christof M. Aegerter "Scattered light fluorescence microscopy: imaging through turbid layers." Optics Letters vol. 35, No. 8: 1245-1247 (Apr. 15, 2010).

I.M. Vellekoop, et al. "Exploiting disorder for perfect focusing." Nature Photonics vol. 4: 320-322 (Feb. 14, 2010).

Noah H. Schwartz, et al. (2009). Mitigation of Atmospheric Effects by Adaptive Optics for Free-Space Optical Communications, Atmospheric Propagation of Electromagnetic Waves III, ed. Olga Korotkova, Proc. of SPIE, vol. 7200, 11 pp.

W.B. Bridges, et al., "Coherent Optical Adaptive Techniques," Appl. Optics vol. 13, No. 2, 291-300 (Feb. 1974).

J.E. Pearson, et al., "Coherent optical adaptive techniques: design and performance of an 18-element visible multidither COAT System," Appl. Optics vol. 15, No. 3, 611-621 (Mar. 1976).

I.M. Vellekoop, et al., "Focusing coherent light through opaque strongly scattering media," Opt. Lett. vol. 32, No. 16, 2309-2311 (Aug. 15, 2007).

N.B. Baranova and B.YA. Zel'Dovich, "Dislocations of the wavefront surface and zeros of the amplitude." Soviet Physics—JETP 53(5): 925-929, (May 1981).

Meng Cui, et al., "Turning Tissues Transparent by Optical Phase Conjugation," Photonics Society Winter Topicals Meeting Series (WTM), 2010 IEEE, pp. 78-79, Jan. 11, 2010.

Jan Huisken, et al., "Optical Sectioning Deep Inside Live Embryos by Selective Plane Illumination Microscopy," Science 305, 1007-1009 (2004).

Brian A. Wilt, et al., "Advances in Light Microscopy for Neuroscience," Annu. Rev. Neurosci. 32, 435-506 (2009).

David Huang, et al., "Optical Coherence Tomography," Science 254, 1178-1181 (1991).

Winfried Denk, et al., "Two-Photon Laser Scanning Fluorescence Microscopy," Science 248, 73-76, Apr. 1990.

Andreas Zumbusch, et al., "Three-Dimensional Vibrational Imaging by Coherent Anti-Stokes Raman Scattering," Phys. Rev. Lett. 82, 4142-4145, May 17, 1999.

Lihong V. Wang, "Multiscale photoacoustic microscopy and computed tomography," Nat. Photonics 3, 503-509, Aug. 28, 2009.

Eric Betzig, et al., "Imaging Intracellular Fluorescent Proteins at Nanometer Resolution," Science 313, 1642-1645, Sep. 15, 2006.

Willy Supatto, et al., "Quantitative imaging of collective cell migration during *Drosophila* gastrulation: multiphoton microscopy and computational analysis," Nat. Protocols 4, 1397-1412, Sep. 10, 2009.

Amnon Yariv, "Phase Conjugate Optics and Real-Time Holography," IEEE J Quantum Elect. 14, 650-660, Sep. 1978.

Claire Gu, et al., "Partial phase conjugation, fidelity, and reciprocity," Opt. Commun. 107, 353-357, May 1, 1994.

Arnaud Derode, et al., "Robust Acoustic Time Reversal with High-Order Multiple Scattering," Phys. Rev. Lett. 75, 4206-4209, Dec. 4, 1995.

Meng Cui, et al., "Observation of polarization-gate based reconstruction quality improvement during the process of turbidity suppression by optical phase conjugation," Appl. Phys. Lett. 95, 123702 (2009).

Geoffroy Lerosey, et al., "Focusing Beyond the Diffraction Limit with Far-Field Time Reversal," Science 315, 1120-1122, Feb. 23, 2007.

Charles A. Primmerman, et al., "Compensation of atmospheric optical distortion using a synthetic beacon," Nature 353, 141-143, Sep. 12, 1991.

Markus Rueckel, et al., "Adaptive wavefront correction in two-photon microscopy using coherence-gated wavefront sensing," P Natl Acad Sci USA 103, 17137-17142, Nov. 14, 2006.

Martin Booth, et al., "Adaptive aberration correction in a confocal microscope," P Natl Acad Sci USA, 99, 5788-5792, Apr. 30, 2002.

Na Ji, et al., "Adaptive optics via pupil segmentation for high-resolution imaging in biological tissues," Nat Meth 7, 141-U184, Feb. 2010.

I.M. Vallekoop, et al., "Focusing light through living tissue," Proc. SPIE 7554, 755430, 2010.

Chia-Lung Hsieh, et al., "Digital phase conjugation of second harmonic radiation emitted by nanoparticles in turbid media," Opt. Express 18, 12283-12290, Jun. 7, 2010.

Austin Roorda, et al., "Adaptive optics scanning laser ophthalmoscopy," Opt. Express 10, 405-412, May 6, 2002.

Delphine Debarre, et al., "Adaptive optics for structured illumination microscopy," Opt. Express 16, 9290-9305, Jun. 23, 2008.

Meng Cui, et al., "An in vivo study of turbidity suppression by optical phase conjugation (TSOPC) on rabbit ear," Opt. Express 18, 25-30, Jan. 4, 2010.

\* cited by examiner

WAVEFRONT CORRECTION OF LIGHT BEAM

CROSS-REFERENCE TO RELATED APPLICATION

This application claims priority to U.S. Application No. 61/434,204, filed on Jan. 19, 2011 and entitled "Focusing Light through Random Scattering Media," which is incorporated herein by reference in its entirety.

TECHNICAL FIELD

The disclosed subject matter relates to a method and system for focusing a light beam through a random scattering medium by determining a wavefront of the light beam and correcting the wavefront of the light beam.

BACKGROUND

When an optical beam from a light source such as a laser passes through a scattering medium such as biological tissue, random elastic scattering can distort and move the optical beam wavefront and any image of the optical beam on a target. Images produced by the optical beam are blurred by these distortions. The wavefront of the optical beam can be considered a surface passing through all points and having the same phase; the wavefront is generally perpendicular to the direction of propagation of the optical beam. The direction of propagation of the optical beam is also referred to as its optic axis.

One technique called adaptive optics has been developed to compensate for these distortions. In traditional adaptive optics, a wavefront sensor can be used to detect the wavefront of the optical beam, and a computer receives the output from the wavefront sensor and corrects for the distortions by reshaping a deformable mirror that lies in the path of the optical beam.

SUMMARY

In one general aspect, a method includes combining a first light beam and a second light beam that are separated from each other by a difference frequency into an interference beam; directing the interference beam onto a random scattering medium; scanning the first light beam transversely to the first optic axis to visit a set of N distinct modes in the spatial frequency domain; detecting measurement light from the random scattering medium during the scanning; analyzing the difference frequency signal of the detected measurement light at each of the N distinct modes to determine the phase and amplitude information in the spatial frequency domain of the detected measurement light; transforming the phase and amplitude information from the spatial frequency domain into the spatial domain; and determining a spatial phase compensation profile to apply to the second light beam.

Implementations can include one or more of the following features. For example, the method can include, after determining the phase compensation profile to apply to the second light beam, applying the spatial phase compensation profile to the second light beam. The method can include, after applying the phase compensation profile to the second light beam, blocking the first light beam so that only the second light beam is directed onto the random scattering medium. The method can include, after blocking the first light beam, performing imaging on the random scattering medium using the second light beam. Imaging on the random scatting medium can be performed by detecting imaging light from the random scattering medium produced by the second light beam. Imaging light from the random scattering medium can be detected by detecting fluorescence produced by the random scattering medium.

Measurement light from the random scattering medium can be detected by detecting fluorescence produced by the random scattering medium during scanning.

The method can include, prior to directing the interference beam onto the random scattering medium, calibrating a scanning optical system that performs scanning of the first light beam relative to a wavefront correction system that applies the spatial phase compensation profile to the second light beam.

The first light beam can be scanned transversely to the first optic axis by scanning the first light beam across a first transverse direction and across a second transverse direction.

The first light beam can be generated and the second light beam can be generated by generating the first light beam and the second light beam from a laser by diffracting the laser output into at least two beams that are shifted in frequency relative to each other.

The method can include generating the first light beam traveling along a first optic axis and operating at a first frequency; and generating the second light beam traveling along a Second optic axis and operating at a second frequency that is distinct from the first frequency by the difference frequency.

In another general aspect, an apparatus includes a transverse scanning optical system, a wavefront correction system, a beam combiner, a detection system, and a control system. The transverse scanning optical system is in the path of a first light beam traveling along a first optic axis, the transverse scanning optical system including a first set of optical elements configured to scan the first light beam along a first direction (X) transverse to the first optic axis and a second set of optical elements configured to scan along a second direction (Y) transverse to the first optic axis. The wavefront correction system is in the path of a second light beam traveling along a second optic axis, the wavefront correction system including a wavefront correction device having a spatial phase profile on its surface. The beam combiner receives the first light beam and the second light beam and outputs an interference beam having a beat frequency equal to a difference frequency, which is the difference in frequency between the first light beam and second light beam. The detection system is placed relative to a random scattering medium, which is in the path of the interference beam, the detection system configured to detect measurement light produced by the random scattering medium while the interference beam strikes the random scattering medium and to detect imaging light produced by the random scattering medium while only the second light beam strikes the random scattering medium. The control system is connected to the transverse scanning optical system, the wavefront correction system, and the detection system.

Implementations can include one or more of the following features. For example, the apparatus can also include a light source outputting the first light beam operating at a first frequency and outputting the second light beam operating at a second frequency that is distinct from the first frequency by the difference frequency.

The control system can be configured to send a signal to the transverse scanning optical system to scan the first light beam transversely to the first optic axis to visit a set of N distinct modes in the spatial frequency domain; receive a signal from the detection system during scanning; analyze the difference frequency signal of the received signal at each of the N distinct modes to determine the phase and amplitude information in the spatial frequency domain of the detected measurement light; transform the phase and amplitude information from the spatial frequency domain into the spatial domain; and output a signal to the wavefront correction device indicating the values of the information in the spatial domain.

The apparatus can include a beam block moveable between a blocking position that is in the path of the first light beam and a non-blocking position that is not in the path of the first light beam.

The transverse scanning optical system can include an X actuator coupled to the first set of optical elements and a Y actuator coupled to the second set of optical elements, wherein the control system is connected to the X and Y actuators of the transverse scanning optical system. The first set of optical elements can include a moveable mirror and the X actuator can include a mirror galvanometer and the second set of optical elements can include a moveable mirror and the Y actuator includes a mirror galvanometer.

The first set of optical elements can include a moveable mirror and the second set of optical elements can include a moveable mirror, and the wavefront correction device can include a spatial light modulator.

The detection system can be configured to detect fluorescence produced by the random scattering medium while the interference beam strikes the random scattering medium and while only the second light beam strikes the random scattering medium. The detection system can be configured to detect backscattering from the random scattering medium while the interference beam strikes the random scattering medium and while only the second light beam strikes the random scattering medium.

The wavefront correction apparatus and method enable imaging in a random scattering medium that produces either a coherent optical signal or an incoherent optical signal. The wavefront correction apparatus and method operate fully without the addition of a wavefront sensor. The wavefront correction apparatus and method of wavefront correction employ a wavefront correction subsystem having enough degrees of freedom to enable wavefront correction in biological tissues, which have refractive index variations that cause more severe wavefront distortion of a light beam than air turbulence. Acquisition time for the wavefront correction apparatus and method can be reduced to about one millisecond (ms) per degree of freedom and still provide for a million degrees of freedom. The wavefront correction apparatus and method has been employed to focus a light beam through a random scattering medium with a 400 ms total data acquisition time, which is three orders of magnitude larger than the speed obtained in previous systems.

DESCRIPTION OF DRAWINGS

FIG. 11b is an exploded view of a section of the graphs of FIG. 11a;

DESCRIPTION

Figure 1:
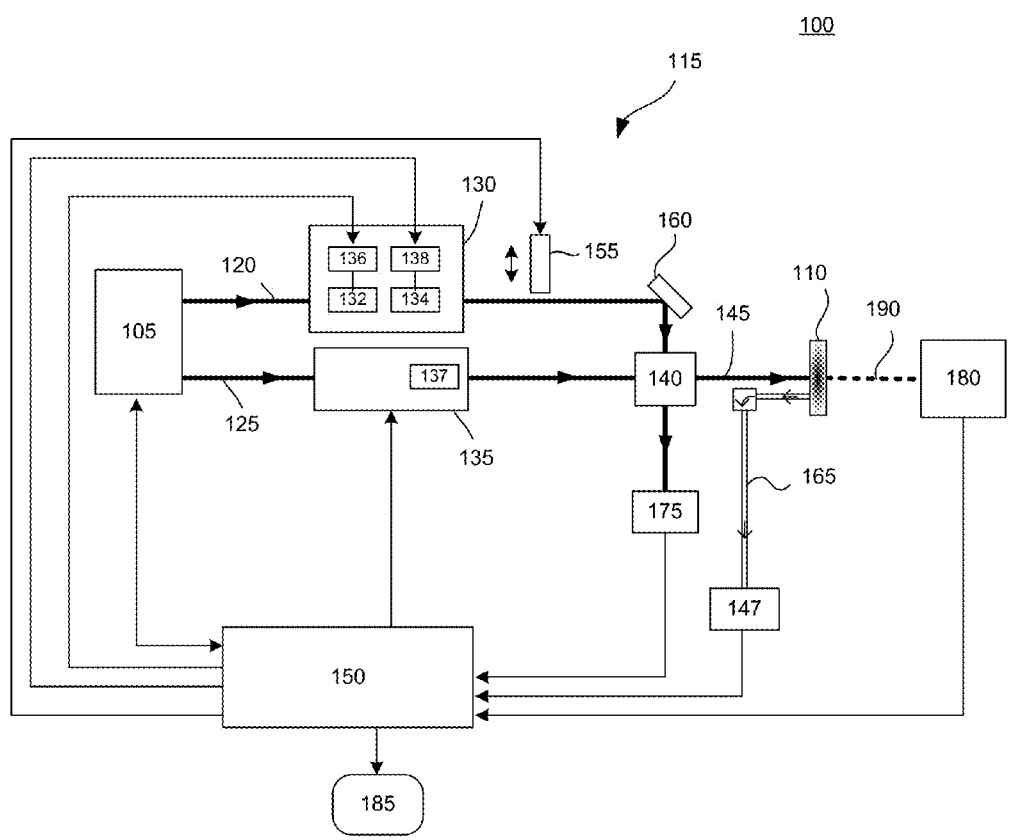
FIG. 1 is a block diagram of an exemplary imaging system for imaging a random scattering medium.
Figure 2:
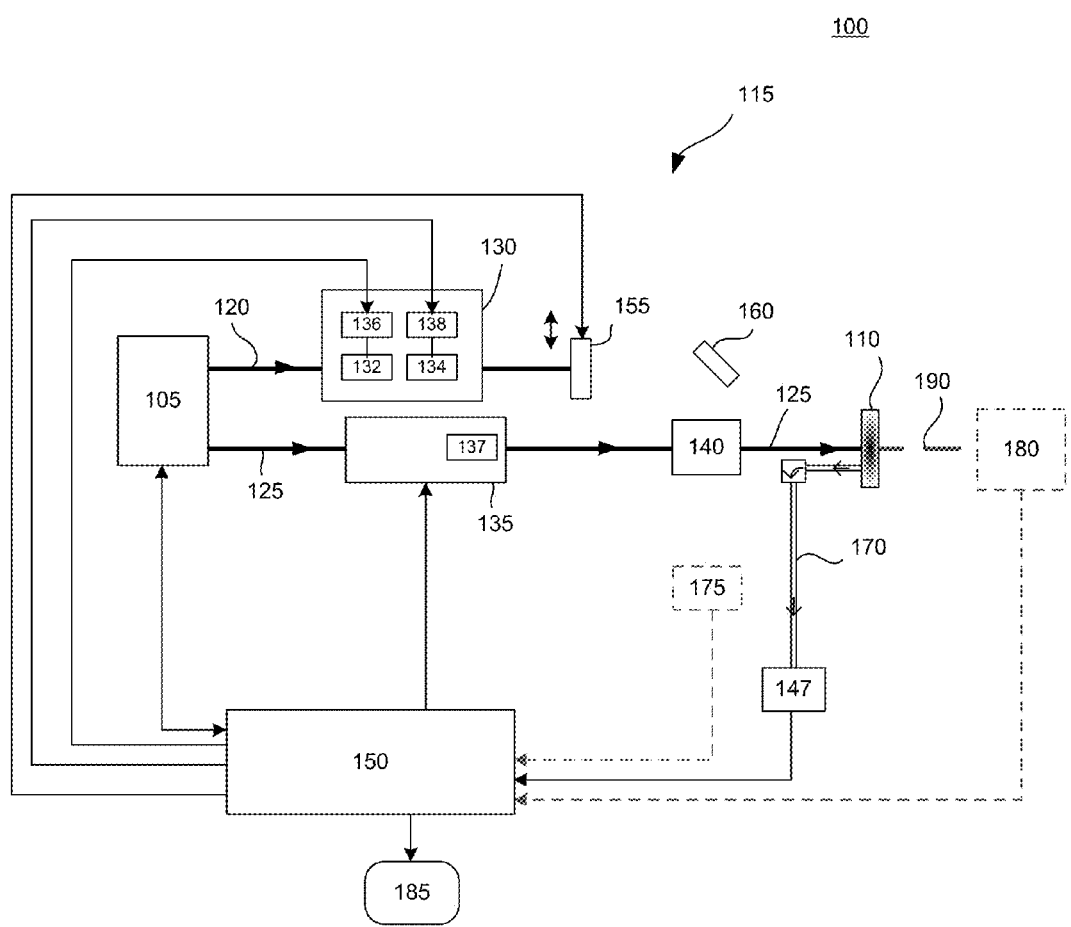
FIG. 2 is a block diagram of the imaging system of FIG. 1 set up for imaging of the random scattering medium.

Referring to FIGS. 1 and 2, an imaging system 100 includes a light source 105 for imaging a random scattering medium 110, and a wavefront correction apparatus 115 within the system 100 for determining the wavefront of the light beam impinging upon the medium 110 to enable the focusing of the light beam through the medium 110. For biological imaging, the random scattering medium 110 is a biological sample or biological material such as biological tissue. The light source 105 produces at least a first light beam 120 traveling generally along a first optic axis and operating at a first frequency f1 and a second light beam 125 traveling along a second optic axis that is distinct from the first optic axis and operating at a second frequency f2 that is distinct from the first frequency by a difference frequency Fd, that is, $Fd=|f1-f2|\neq 0$. The difference frequency Fd is tunable, as described in greater detail below with reference to specific implementations of the imaging system 100. The light source 105 can be any combination of optical components that work together to produce the two light beams 120, 125. In specific implementations discussed herein, the light source 105 includes, among other components, a coherent source such as a laser (for example, a continuous wave laser) and acousto-optic modulators (AOM) at the output of the laser to produce two frequency shifted beams 120, 125.

The wavefront correction apparatus 115 includes the following components: a transverse scanning optical system 130 in the path of the first light beam 120, a wavefront correction system 135 in the path of the second light beam 125, a beam combiner 140 that receives the first, light beam and the second light beam and outputs an interference light beam 145 toward the medium 110; a detection system 147, and a control system 150.

The wavefront correction apparatus 115 also includes a beam block 155 that is moveable between a blocking position that is in the path of the first light beam 120 (shown in FIG. 2) and a non-blocking position that is not in the path of the first light beam 120 (shown in FIG. 1). Thus, when the beam block 155 is in the non-blocking position, the first light beam 120 and the second light beam 125 are both directed to the beam combiner 140, which produces the interference beam 145 (FIG. 1), and when the beam block 155 is in the blocking position, only the second light beam 125 is directed to the beam combiner 140, which simply outputs the second light beam 125 toward the medium 110 (FIG. 2).

The wavefront correction apparatus 115 may also include additional optic devices such as mirrors, corner cubes, lenses, lens relays, prisms, etc. to steer or shape one or more of the first and second light beams 120, 125. As shown in this example, a mirror 160 is placed in the path of the first light beam 120 to steer the first light beam 120 toward the beam combiner 140. In other implementations discussed herein, these additional optic devices include other mirrors and relays.

The transverse scanning optical system 130 includes a first set of optical elements 132 configured to scan the first light beam 120 along a first direction (X) that is transverse to the first optic axis and a second set of optical elements 134 configured to scan the first light beam 120 along a second direction (Y) that is transverse to the first optic axis. The first and second directions are distinct from each other and can be orthogonal to each other in some implementations. The optical elements 132, 134 can include one or more moveable (for example, rotatable) specular reflective devices such as mirrors or corner reflectors, and moveable refractive devices such as prisms. In the implementations discussed and shown below, the first set of optical elements 132 includes a rotatable mirror and the second set of optical elements 134 includes a rotatable mirror.

Additionally, the transverse scanning optical system 130 includes an X actuator 136 coupled to the first set of optical elements 132 and a Y actuator 138 coupled to the second set of optical elements 134. The actuator 136, 138 can be any suitable actuator that converts an electrical signal from the control system 150 into a mechanical movement imparted to the optical elements 132, 134. Thus, the actuators 136, 138 can be electro-mechanical, electro-optical, acousto-optical, etc. Specific implementations of the transverse scanning optical system 130 are described in detail below in which the X actuator 136 is a mirror galvanometer and the Y actuator 138 is a mirror galvanometer. In other implementations, the actuators 136, 138 could include resonant scanning mirrors, polygon mirror scanners, acousto-optic deflectors, and electro-optic deflectors.

The wavefront correction system 135 that is in the path of the second light beam 125 can include one or more components such as lenses, lens relays, and mirrors, for directing and shaping the second light beam 125, and a wavefront correction device 137 that has a spatial profile on its surface to enable wavefront correction of the second light beam 125.

The wavefront correction device 137, specific implementations of which are described below, can be any device that controls and modulates the wavefront of the second light beam 125. For example, the wavefront correction device 137 can be a spatial light modulator (SLM) that modulates the spatial phase of the second light beam 125. The SLM can be reflective or transmissive depending on the application. Suitable SLMs can be purchased from, for example, Boulder Nonlinear Systems of Lafayette, Colo., United States or HOLOEYE Photonics AG of Berlin-Adlershof, Germany. As another example, the wavefront correction device 137 can be a deformable mirror having a response time as low as microseconds. Such deformable mirrors can be purchased from Boston Micromachines Corporation of Cambridge, Mass., United States, or from Fraunhofer Institute for Photonic Microsystems of Dresden, Germany.

The beam combiner 140 combines the first light beam 120 with the second light beam 125 such that the light beams 120, 125 interfere with each other to form the interference light beam 145. In some implementations, the beam combiner 140 includes a 50:50 beam splitter.

The detection system 147 can be placed relative to the random scattering medium 110 to receive measurement light 165 produced by the random scattering medium 110 while the interference light beam 145 strikes the random scattering medium 110 (as shown, for example, in FIG. 1) and to detect imaging light 170 produced by the random scattering medium 110 while only the second light beam 125 strikes the random scattering medium 110 (as shown, for example, in FIG. 2). The measurement light 165 and the imaging light 170 can be any light produced at the random scattering medium 110 after it is struck by the interference light beam 145 or the second light beam 125, respectively. For example, the measurement light 165 and the imaging light 170 can be a backward signal (reflected) or a forward signal (transmitted), or can be from fluorescence of fluorophores within the random scattering medium 110, or can be scattering light from the random scattering medium 110.

The control system 150 is connected to the X and Y actuators 136, 138 of the transverse scanning optical system 130, to the wavefront correction system 135, and to the detection system 147.

Additionally, the control system 150 can be connected to the light source 105, a calibration detector 175, a diagnostic and testing apparatus 180, and a diagnostic and testing output device 185 such as a display. As discussed in greater detail herein, the diagnostic and testing apparatus 180 can be used to analyze a test light beam 190 that is produced while using a random scattering medium such as a diffuser.

Figure 3:
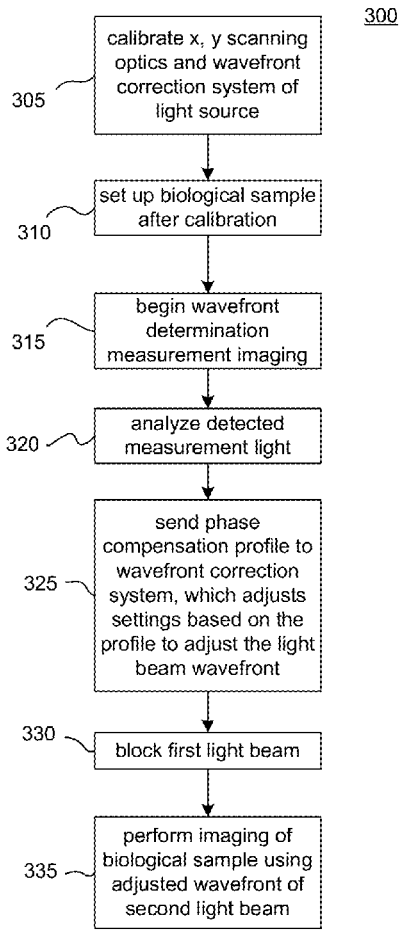
FIG. 3 is a flow chart of a procedure performed by the imaging system of FIGS. 1 and 2 for correcting a wavefront of a light beam impinging upon the random scattering medium.
Figure 10:
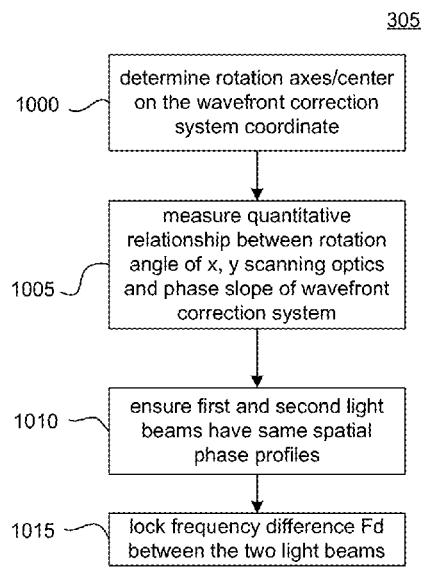
FIG. 10 is a flow chart of a procedure performed by the control system of the imaging system of FIG. 9.
Figure 4:
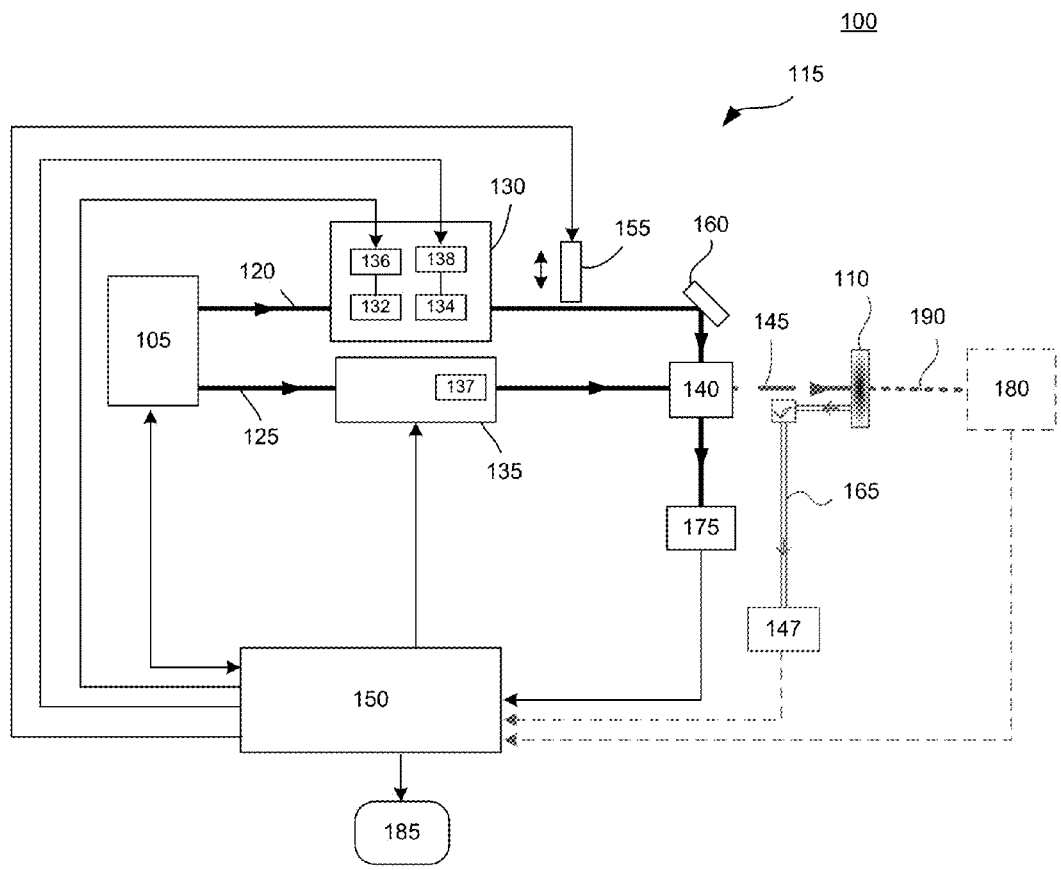
FIG. 4 is a block diagram of the imaging system of FIG. 1 set up for calibration of the components of the imaging system.
Figure 9:
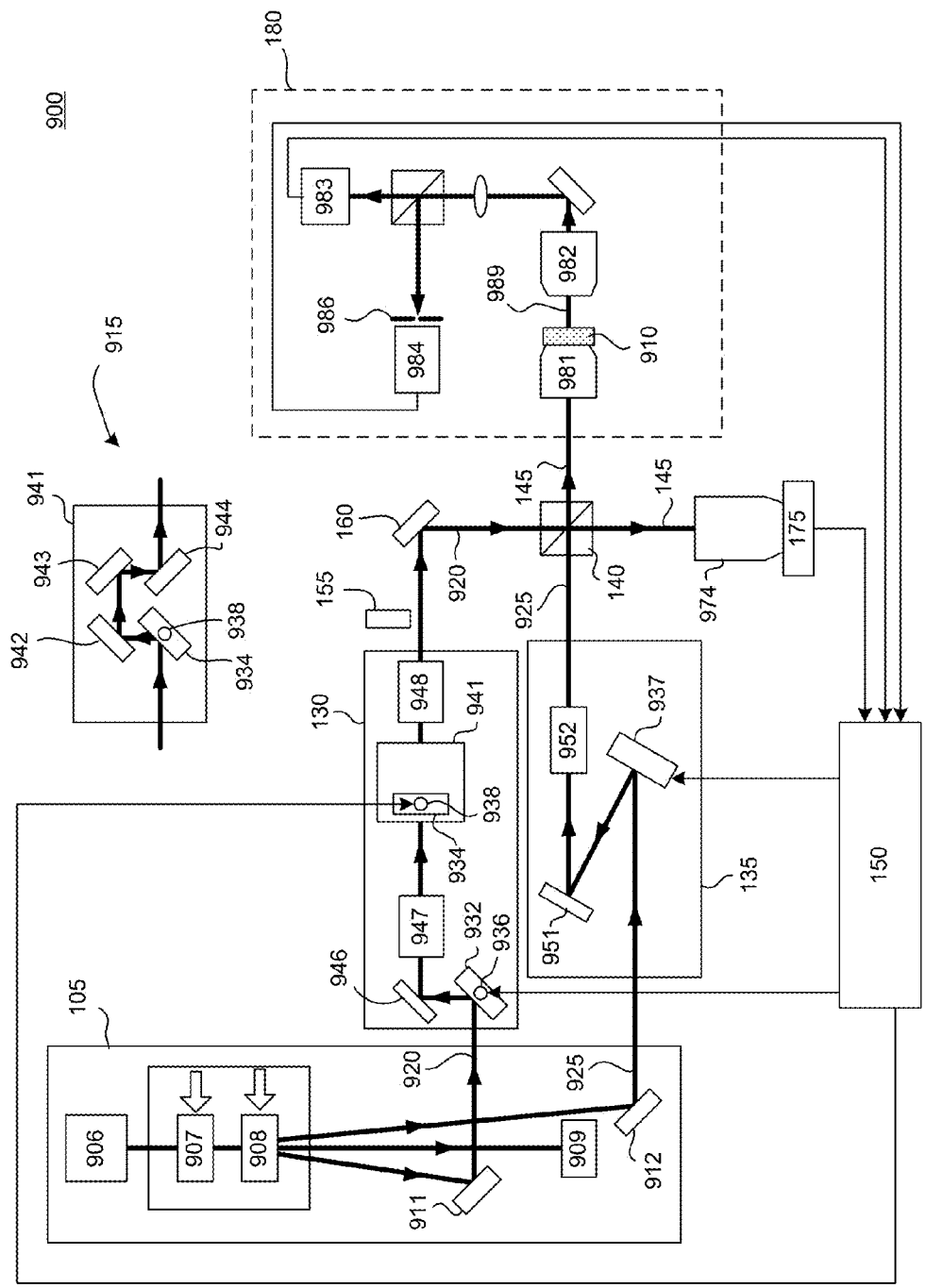
FIG. 9 is a block diagram of an exemplary imaging system set up for calibration and testing.

Referring to FIG. 3, a procedure 300 is performed for imaging a random scattering medium 110 such as a biological sample and for producing a high quality focus through the random scattering medium 110 by determining a wavefront based on spatial frequency domain wavefront modulations using the imaging system 100. Initially, the optics within the transverse scanning optical system 130 and the wavefront correction system 135 of the wavefront correction apparatus 115 are calibrated using the output from the calibration detector 175 and the control system 150 (step 305), the set-up of which is shown generally in FIG. 4. In FIG. 4, the components of the imaging system 100 that are inactive during calibration are grayed out and dashed. Moreover, a specific implementation of a set-up for the calibration is shown in FIG. 9 and is described with reference to the procedure 305 shown in FIG. 10, as discussed below.

Once the calibration is complete, the calibration detector 175 becomes inactive, and the random scattering medium 110

(which, in the implementations described, is a biological sample 110) is set up in the path of the interference light beam 145 (step 310).

Figure 5:
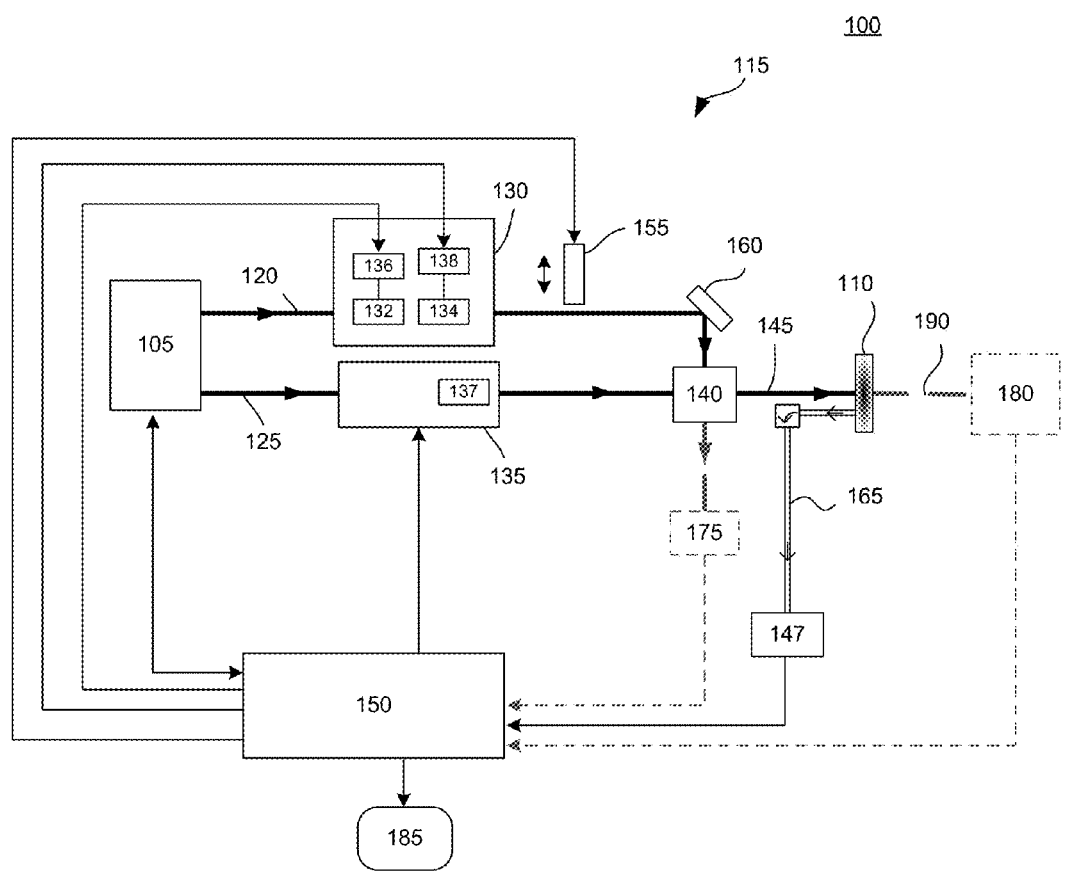
FIG. 5 is a block diagram of the imaging system of FIG. 1 set up for a wavefront determination measurement.
Figure 13:
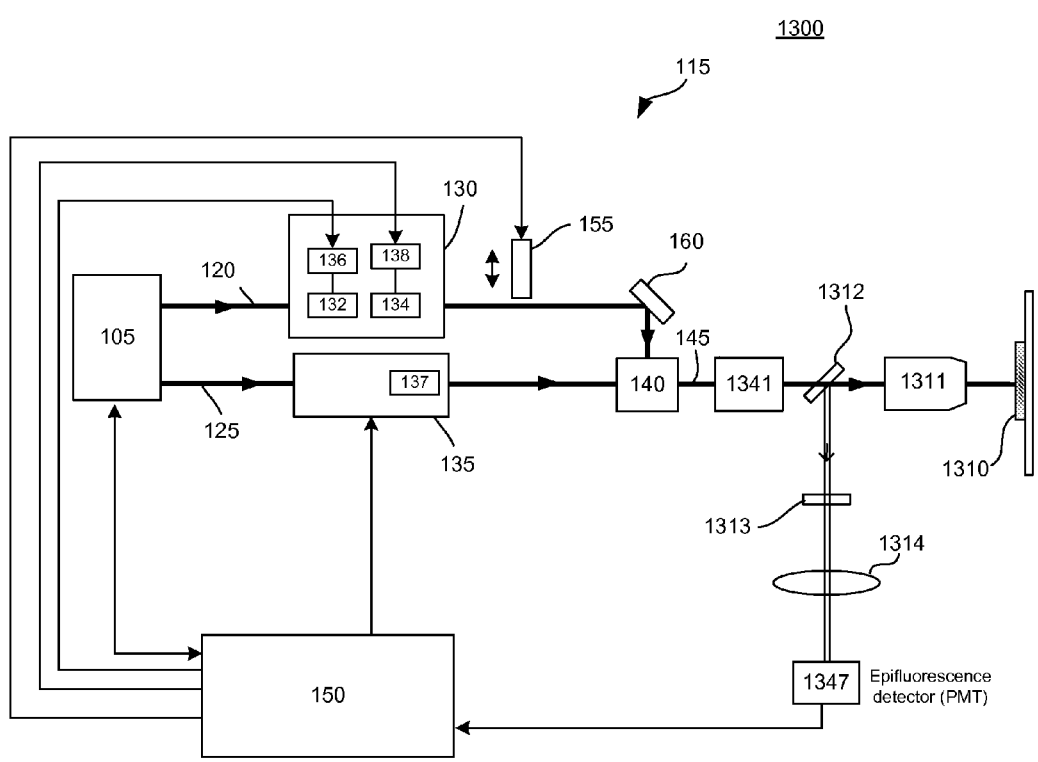
FIG. 13 is a block diagram of an exemplary fluorescence imaging system showing components used for the wavefront determination measurement and fluorescence imaging.
Figure 14:
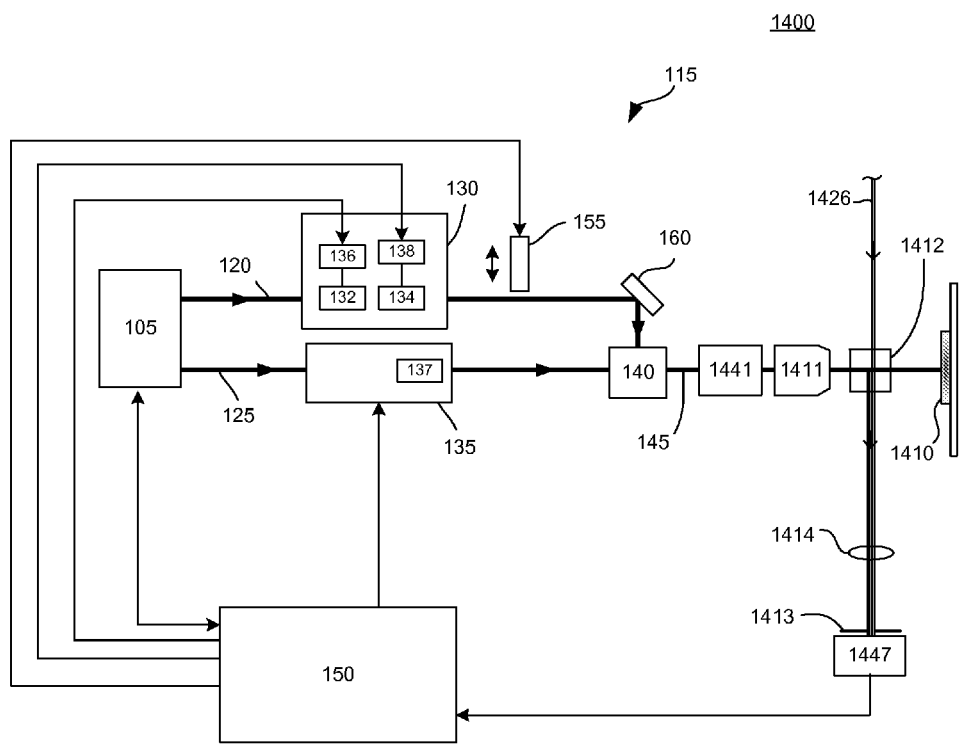
FIG. 14 is a block diagram of an exemplary backscattering imaging system showing components used for the wavefront determination measurement and backscattering imaging.

Next, the wavefront determination measurement begins (step 315) using the interference light beam 145 and the detection system 147, the set-up of which is shown generally in FIG. 5. In FIG. 5, the components of the imaging system 100 that are inactive during the wavefront determination measurement (step 315) are grayed out and dashed. Additionally, specific implementations of the set-up for the wavefront determination measurement are shown in FIGS. 13 and 14 and are described below.

Figure 6:
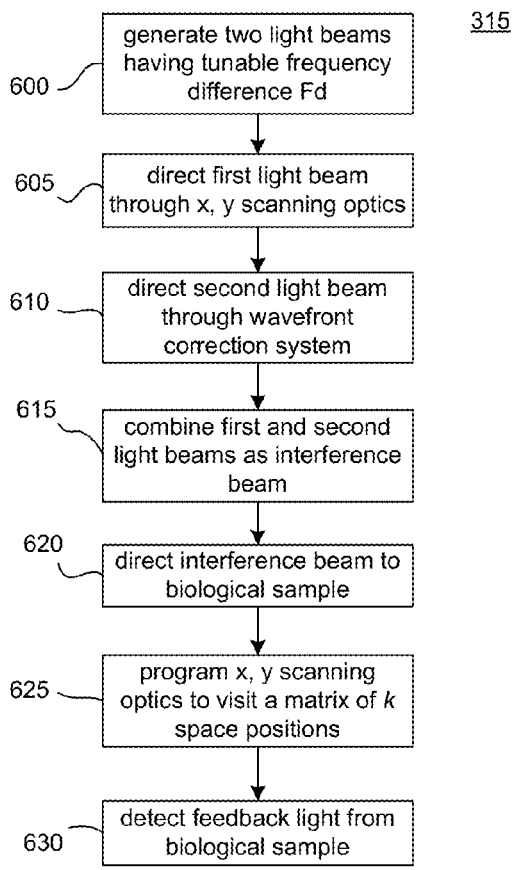
FIG. 6 is a flow chart of a procedure performed by the imaging system of FIGS. 1, 2, 4, and 5 for a wavefront determination measurement.

During the wavefront determination measurement, a procedure 315 shown in FIG. 6 is performed. In particular, the light source 105 generates the first light beam 120 and the second light beam 125, and enables tuning of the difference frequency Fd between the beams 120, 125 (step 600). The first light beam 120 is directed through the transverse scanning optical system 130 (step 605) and the second light beam 125 is directed through the wavefront correction system 135 (step 610). The first light beam 120 output from the transverse scanning optical system 130 and the second light beam 125 output from the wavefront correction system 135 are combined at and by the beam combiner 140 such that they interfere with each other and produce the interference light beam 145 (step 615). The interference light beam 145 is directed, using suitable optics, toward the biological sample 110 (step 620). Moreover, the control system 150 scans the first light beam 120 to visit a matrix of distinct modes in the spatial frequency (kx, ky) domain while the interference light beam 145 strikes the biological sample 110 (step 625), and the detection system 147 detects the measurement light 165 that is produced at the biological sample 110 while the interference light beam 145 strikes the biological sample 110 (step 630). The distinct modes in the spatial frequency domain may or may not be uniformly distributed.

Figure 7:
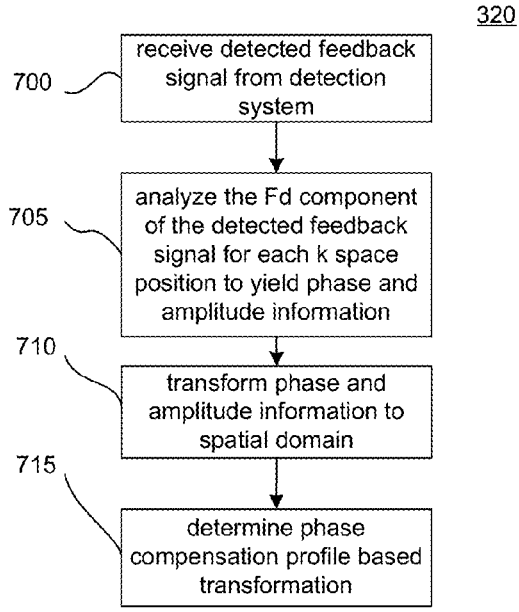
FIG. 7 is a flow chart of a procedure performed by a control system within the imaging system of FIGS. 1, 2, 4, and 5 for analyzing detected measurement light obtained from the random scattering medium.

Referring again to FIG. 3, the control system 150 analyzes the detected measurement light 165 from the detection system 147 (step 320). During this analysis, a procedure 320 shown in FIG. 7 is performed by the control system 150. Initially, the control system 150 receives the output (that is, the detected feedback signal) from the detection system 147 (step 700). Next, the control system 150 analyzes the Fd component of the detected feedback signal for each k space position to yield the phase φ (kx, ky) and the amplitude A (kx, ky) in k space (step 705). The control system 150 transforms the phase and amplitude in k space into the spatial domain to generate the spatial phase information E (x, y) (step 710) and determines the phase compensation profile for the wavefront of the second light beam 125 based on the transformation (step 715). If the kx and ky modes are uniformly distributed, then the control system 150 performs a fast Fourier transform (FFT) to generate the spatial phase information E (x, y). On the other hand, if the kx and ky modes are not uniformly distributed, then the control system 150 can determine E (x, y) using the following formula:

$$E(x, y) = \sum_{k_x, k_y} A_{k_x, k_y} e^{i(k_x x + k_y y + \varphi_{k_x, k_y})}.$$

Figure 8A:
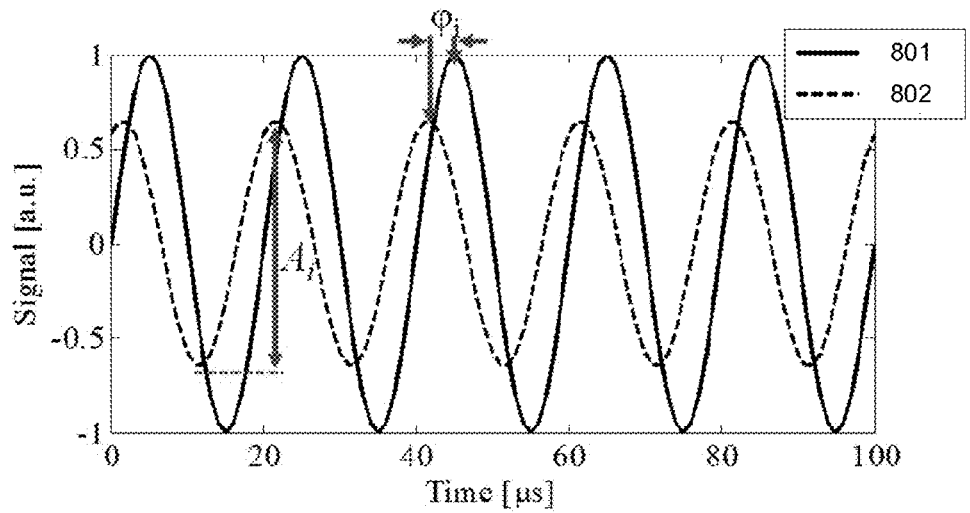
FIG. 8a is a graph showing the interference beam signal produced by the imaging system of FIG. 1 versus time as detected at a calibration detector.

Referring to FIG. 8a, a graph 801 is shown that illustrates the signal (in arbitrary units) of the interference beam 145 versus time (in μs in the example shown) as would be detected at the calibration detector 175. Thus, the graph 801 shows an exemplary shape of the interference beam 145 that would strike the biological sample 110. The graph 801 shows that the difference frequency Fd between the two beams 120, 125 is 50 kHz in this particular example. The graph 802 shows an exemplary illustration of the signal (in arbitrary units) as measured at the detection system 147 during the wavefront determination measurement versus time superimposed upon the graph 801 to show the relationship between these signals.

Figure 8B:
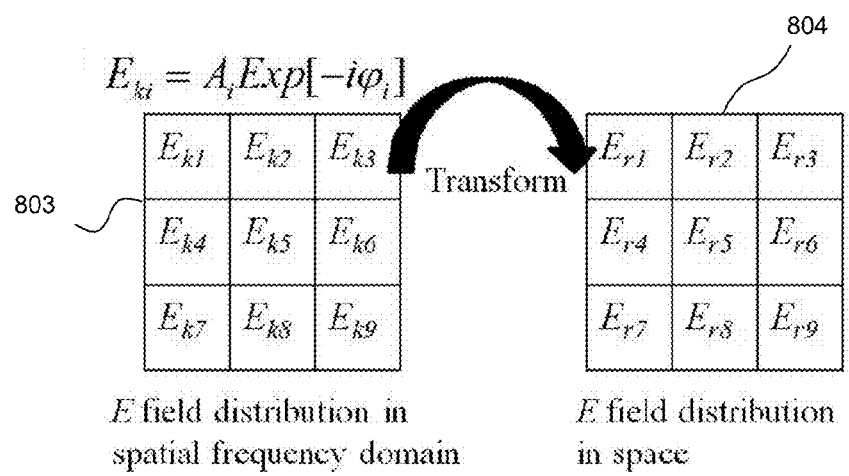
FIG. 8b is a schematic illustration showing an exemplary first matrix of modes in the spatial frequency domain transformed into a second matrix in the spatial domain by a control system of the imaging system of FIG. 1.

Referring to FIG. 8b, the values of the phase φ (kx, ky) and the amplitude A (kx, ky) in k space that are determined during step 705 are shown in an exemplary 3×3 array 803, and at the end of the measurement, these values are transformed into the spatial domain, as shown in the exemplary array 804. This spatial profile is sent to the wavefront correction device 137 to adjust the wavefront of the second light beam 125 that will be used to image the biological sample 110 in application.

Referring again to FIG. 3, the control system 150 sends the phase compensation profile to the wavefront correction system 135, and in particular, to the wavefront correction device 137, which adjusts its settings based on the profile to adjust the wavefront of the second light beam 125 (step 325). The first light beam 120 is blocked using the beam block 155 (step 330). The beam block 155 can be moved manually or can be moved by the control system 150 (as shown in FIGS. 1 and 2).

Once the first light beam 120 is blocked (step 330), the imaging system 100 performs imaging of the biological sample 110 using the adjusted wavefront of second light beam 125, as shown in FIG. 2.

Referring to FIG. 9, an exemplary imaging system 900 that is set up for calibration (step 305) is shown. Also shown in the imaging system 900 is, a diagnostic and testing apparatus 180 that will be described below; the apparatus 180 demonstrates the feasibility of the imaging system 900 on a test random scattering medium 110, which, in the example described, is a diffuser 910.

In the imaging system 900, the light source 105 includes a continuous wave laser 906 that outputs a primary beam and a pair of acousto-optic modulators (AOMs) 907, 908 that are placed in serial along the path of the primary beam to provide for two frequency-shifted beams, the first light beam 920 and the second light beam 925. The AOMs 907, 908 are aligned to optimize the diffraction for 50 MHz acoustic waves. The zeroth ($0^{th}$) order beam is blocked by a beam block 909, the first light beam 920 is redirected by a mirror 911 toward the transverse scanning optical system 130, and the second light beam 925 is redirected by a mirror 912 toward the wavefront correction system 135.

The transverse scanning optical system 130 includes, as the first set of optical elements 132, a moveable mirror 932, which is moveable (for example, rotatable) by a mirror galvanometer 936, and, as the second set of optical elements 134, a moveable mirror 934, which is moveable (for example, rotatable) by a mirror galvanometer 938. In particular, the moveable mirror 932 is moveable in such a way as to scan the first light beam 920 along the X transverse direction, and the moveable mirror 934 is moveable in such a way as to scan the second light beam 925 along the Y transverse direction. The moveable mirror 934 is a part of an optical fold layout 941 that includes three folding mirrors 942, 943, 944, which fold the first light beam 920 back to the X plane. The transverse scanning optical system 130 also includes other optical elements for shaping and redirecting the first light beam 920 such as, for example, a mirror 946, and lens relays 947, 948.

The wavefront correction system 135 includes, as the wavefront correction device 137, a phase-only reflective spatial light modulator (SLM) 937. The wavefront correction system 935 also includes other optical elements for shaping and redirecting the second light beam 925 such as, for example, a mirror 951 and a lens relay 952.

The beam combiner 140 is a 50:50 beam splitter, which combines the first light beam 920 and the second light beam 925 to form the interference light beam 145. During calibration, the interference light beam 145 is directed toward a camera lens 974 onto the calibration detector 175, the output of which is sent to the control system 150. In other implementations, components (such as the calibration detector 983) of the diagnostic and testing apparatus 180 could be used during calibration by removing the diffuser 910 that is used for testing.

In some implementations, the calibration detectors 175 and 983 can be 8-bit cameras, which can be charge-coupled devices (CCDs). During testing, the interference light beam 145 is directed to a photodiode detector 984 within the diagnostic and testing apparatus 180, which is discussed in greater detail following the description of the calibration set up and procedure.

Referring also to Fig, 10, a procedure 305 is performed by the imaging system 900 to calibrate the wavefront correction system 135 and the transverse scanning optical system 130. Initially, the rotation axes of the mirrors 932, 934 and the rotation center are determined on the coordinates of the SLM 937 (step 1000). To do this, the relayed image of the first light beam 920 and the second light beam 925 are imaged by the camera lens 974 onto the calibration detector 175. The AOMs 907, 908 are driven by a two-channel function generator, each channel running at 50 MHz (with no beating). Then, the interference light beam 145 is observed by the calibration detector 175. The mirror 932 is rotated, causing a variation of the interference pattern except for a stationary line, which indicates the rotation axis of the mirror 932. Similarly, the mirror 934 is rotated, causing a variation of the interference pattern except for a stationary line, which indicates the rotation axis of the mirror 934. The intersection of the two rotation axes is the rotation center.

Also, the quantitative relationship between the rotation angle of the mirrors 932, 934 and the phase slope of the SLM 937 is measured (step 1005). To perform this step, the interference light beam 145 can be observed by the calibration detector 175, the output of which is sent to the control system 150. The variation of the interference pattern caused by rotation of the mirrors 932, 934 and the phase slope of the SLM 937 is measured by observing movement of a focus on the calibration detector 175. It should be noted that this step could be performed by components within the diagnostic and testing apparatus 180. Thus, in another implementation, the interference light beam 145 is observed by the calibration detector 983 by removing the diffuser 910 and imaging the focus of the objective 981 onto the detector 983. Rotations of the mirrors 932, 934 and the phase slope of the SLM 937 can move the focus on the detector 983, and the control system 150 can compare the measured movement to obtain the relationship between the mirror rotation and the SLM phase slope.

Moreover, the spatial phase difference between the first light beam 920 and the second light beam 925 is determined to ensure that the beams 920, 925 have the same spatial phase profile (step 1010) because the first light beam 920 is used during wavefront measurement imaging and the determined phase profile from the wavefront measurement imaging is transferred to the second light beam 925. One way to perform this step includes offsetting the mirrors 932, 934 from their center positions to perform a digital off-axis holography and then determining the spatial phase difference between the first light beam 920 and the second light beam 925 using Fourier transform analysis. Another way to perform this step includes performing phase shifting holography by setting the mirrors 932, 934 to their center positions and beating the first light beam 920 and the second light beam 925 at a rate that is a fraction (for example, a quarter) of a frame rate of the calibration detector 175; in this case, four consecutive frames can be used to determine the phase profile.

Additionally, the difference frequency Fd should be locked to a clock that controls the data acquisition (step 1015). In particular, a data acquisition card is configured to output a pulse train (in this case, of 10 MHz) to a reference input of the two-channel function generator that drives the AOMs 907, 908 to tightly synchronize a timing of the data acquisition and the beating between the two beams, that is, the difference frequency Fd.

With reference again to FIG. 3, once the procedure 305 is completed, the wavefront correction system 135 and the transverse scanning optical system 130 have been calibrated and are ready to use for the wavefront determination measurement (step 315).

Though an optional feature, an exemplary diagnostic and testing apparatus 180 is described next to show that the imaging system 900 performs as expected and to demonstrate the procedure with the use of a non-biological sample, namely, the diffuser 910. During testing/diagnostics, the interference beam 145 is relayed to a rear pupil plane of a 20× objective 981 having a numerical aperture NA of 0.5. In one exemplary configuration, the diffuser 910 is a 1.6 mm thick glass diffuser, which is placed in front of the objective 981. The light beam 989 transmitted through the diffuser 910 is collected by a 100× objective 982 having a numerical aperture NA of 0.9 and then imaged onto a photodiode detector 984 with a 100 kHz bandwidth. A 50 micron diameter pinhole 986 is mounted on the detector 984 to limit the collection of the light at the detector 984 to a 500 nm diameter area on the focal plane of the 20× objective 981.

During testing, the light beam 989 transmitted through the diffuser 910 is detected by the photodiode detector 984 as a target signal. The control system 150 sends a signal to the mirror galvanometers 936, 938 to rotate the mirrors 932, 934, respectively, from −0.12° to 0.12° in 20 steps such that 400 k space positions are visited during the testing measurement. The time spent at each position is 1 ms. In the first 400 μs, the mirrors 932, 934 are moving and therefore are in transition from a previous position to a current position. However, in the latter 600 μs of the time, the positions of the mirrors 932, 934 are stable. During testing, feedback signals sent from the control system 150 to the galvanometers 936, 938 that control the mirrors 932, 934 and the target signal taken at the photodiode detector 984 are recorded by the control system 150 for diagnostic purposes. These signals can be digitized at 1 MHz.

Figure 11A:
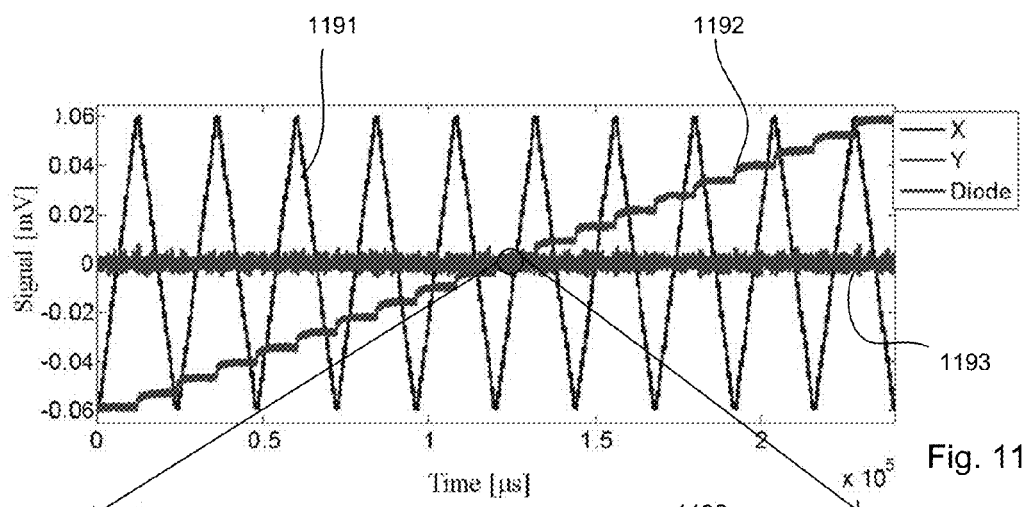
FIG. 11a is a graph of a scanning signal sent to a first mirror actuator versus time; a graph of a scanning signal sent to a second mirror actuator versus time; and a graph of a third signal obtained by a testing detector versus time as the scanning signals are sent to the first and second mirror actuators.
Figure 11B:
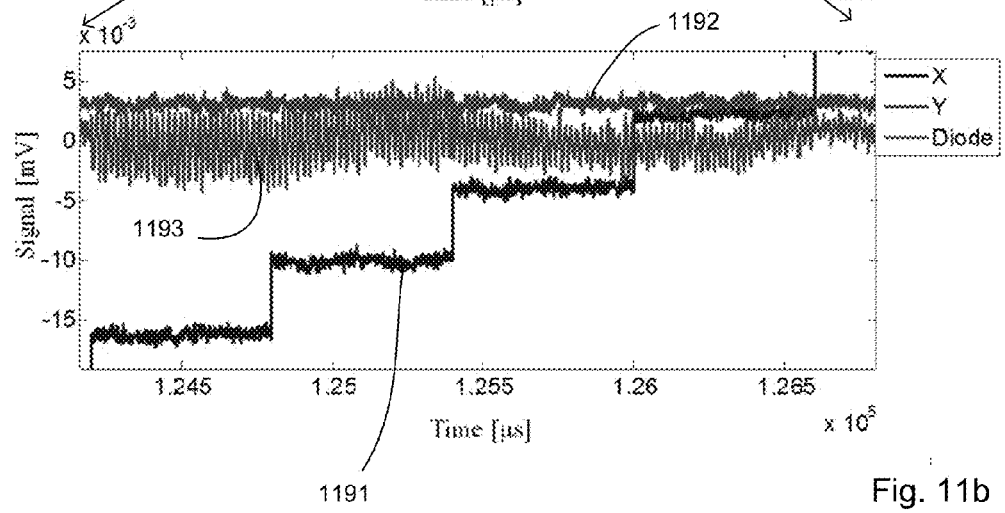

Referring to FIG. 11a, a graph 1191 shows the signal sent to the galvanometer 936 versus time; this signal shows how the mirror 932 is moved in 20 steps for each fixed location of the mirror 934. A graph 1192 shows the signal sent to the galvanometer 938 versus time; this signal shows how the mirror 934 is moved in 20 steps for each fixed location of the mirror 932. In this way, 400 k space positions are visited during the testing measurement. A graph 1193 shows the raw data recorded at the photodiode detector 984 while the mirrors 932, 934 are scanned through the 400 k space positions. FIG. 11b shows an exploded view of a center section of the graphs 1191, 1192, 1193, and the 50 kHz oscillation is evident in the graph 1193.

Figures 12A, 12B, 12C:
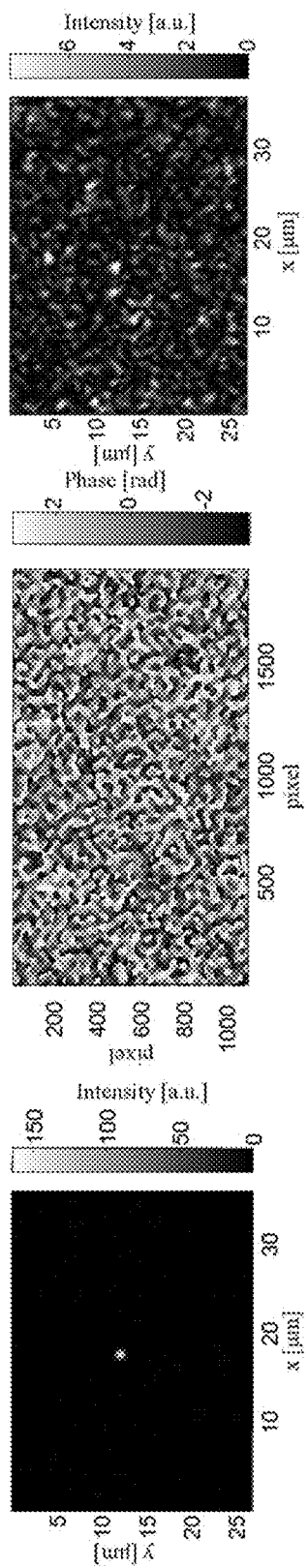
FIG. 12a is an image of an intensity profile observed by a testing detector used in the imaging system of FIG. 9, with wavefront correction applied to a second light beam that is directed to a test random scattering medium.
FIG. 12b is an image of a compensation wavefront profile applied to a spatial light modulator (SLM) of the imaging system of FIG. 9.
FIG. 12c is an image of the intensity profile observed by a testing detector used in the imaging system of FIG. 9 without wavefront correction applied to the second light beam that is directed to the test random scattering medium.

This raw data is divided into 400 arrays, with each data array of spatial frequency values Fourier transformed, extracting the 50 kHz signal (the difference frequency Fd in this example) (step 705), and transforming this to the spatial domain (step 710). The control system 150 sends the phase compensation profile to the SLM 937, which adjusts its reflective surface to control the wavefront of the second light beam 925. At this point, the first light beam 920 is blocked; and a transmission intensity profile (with wavefront compensation applied to the second light beam 925) is observed on the CCD 983, as shown in FIG. 12a; a bright round focus is seen, which indicates that the imaging system 900 has compensated for the random scattering within the diffuser 910. FIG. 12b shows an intensity profile of a compensated wavefront displayed on the SLM 937 during this test, and FIG. 12c shows an intensity profile observed on the CCD 983 without any wavefront compensation displayed on the SLM 937 (this can be taken while the first light beam 920 is blocked). Thus, without the wavefront compensation applied using the imaging system 900, the transmission through the diffuser 910 is a random speckle.

Referring to FIG. 13, a fluorescence imaging system 1300 is shown that uses the design described above, thus, components of the wavefront correction apparatus 115 are included in the imaging system 1300. In a specific implementation, the wavefront correction apparatus 115 in this system 1300 could be designed like the apparatus 915 shown in FIG. 9. The imaging system 1300 is shown after calibration (step 305) is performed, but calibration could be performed on the system 1300, as described above with reference to FIGS. 1, 4, and 9.

In the imaging system 1300, a biological sample 1310 is set up for imaging (step 310). In this case, standard optical components would be added to this system 1300 to perform fluorescence imaging of the biological sample 1310 in combination with the wavefront determination measurement. In particular, the system 1300 includes an objective 1311 that focuses the interference light beam 145 through the sample 1310 during the wavefront determination measurement (steps 310-325) and focuses the second light beam 125 through the sample 1310 during fluorescence imaging (step 335) after the first light beam 120 is blocked (step 330). The system 1300 includes a dichroic mirror or other suitable optic 1312 and a filter 1313 that block light centered around the wavelength of the second light beam 125 during fluorescence imaging (step 335) to ensure that the fluorescence signal that reaches the epifluorescence detector 1347 excludes other light that can cause noise in the signal. The epifluorescence detector 1347 can be a photomultiplier tube (PMT) in this example. Fluorescence light emitted from the biological sample 1310 is collected using a wide area lens 1314.

The imaging system 1300 also includes a transverse scanning optical system 1341, which can be a set of X, Y mirrors controlled by mirror galvanometers. The transverse scanning optical system 1341 scans the second light beam 125 across the sample 1310 during imaging.

Referring to FIG. 14, a backscattering imaging system 1400 is shown that uses the design described above, thus, components of the wavefront correction apparatus 115 are included in the imaging system 1400. In a specific implementation, the wavefront correction apparatus 115 in this system 1400 could be designed like the apparatus 915 shown in FIG. 9. The imaging system 1400 is shown after calibration (step 305) is performed, but calibration could be performed on the system 1400, in the manner that was described above with reference to FIGS. 1, 4, and 9.

In the imaging system 1400, a biological sample 1410 is set up for imaging (step 310). In this case, standard optical components would be added to this system 1400 to perform backscattering imaging of the biological sample 1410 in combination with the wavefront determination measurement. In particular, the system 1400 includes an objective 1411 that collects the interference light beam 145 and directs it toward the biological sample 1410 during the wavefront determination measurement (steps 310-325). Once the wavefront is determined, backscattering imaging begins (step 335) after the first light beam 120 is blocked and the wavefront of the second light beam 125 is corrected. The second light beam 125 is then directed to the sample 1410, and a backscattering signal produced by light reflecting from the sample 1410 is combined with a reference light beam 1426, which is produced by the light source 105, at a beam combiner 1412, and this combined beam gives rise to an interference pattern. This combined beam is shaped by a collection lens 1414 and directed through a pinhole 1413 onto a photodiode detector 1447, the output of which is sent to the control system 150. It should be noted that during the wavefront determination measurement (steps 310-325), the reference light beam 1426 is used. Data can be collected by the detector 1447 using, for example, optical coherence tomography (OCT) techniques or optical coherence microscopy (OCM) techniques.

The imaging system 1400 also includes a transverse scanning optical system 1441, which can be a set of X, Y mirrors controlled by mirror galvanometers. The transverse scanning optical system 1441 scans the second light beam 125 across the sample 1410 during imaging.

Other implementations are within the scope of the following claims.

What is claimed is:

1. A method comprising:
    combining a first light beam traveling along a first optic axis and a second light beam traveling along a second optic axis, the first light beam and the second light beam being separated from each other by a difference frequency, into an interference beam;
    directing the interference beam onto a random scattering medium;
    scanning the first light beam transversely to the first optic axis to visit a set of N distinct modes in a spatial frequency domain;
    detecting measurement light from the random scattering medium during the scanning;
    analyzing a difference frequency signal of the detected measurement light at each of the N distinct modes to determine phase and amplitude information in the spatial frequency domain of the detected measurement light;
    transforming the phase and amplitude information from the spatial frequency domain into a spatial domain; and
    determining a spatial phase compensation profile to apply to the second light beam.

2. The method of claim 1, further comprising, after determining the phase compensation profile to apply to the second light beam, applying the spatial phase compensation profile to the second light beam.

3. The method of claim 2, further comprising, after applying the phase compensation profile to the second light beam, blocking the first light beam so that only the second light beam is directed onto the random scattering medium.

4. The method of claim 3, further comprising, after blocking the first light beam, performing imaging on the random scattering medium using the second light beam.

5. The method of claim 4, wherein performing imaging on the random scatting medium includes detecting imaging light from the random scattering medium produced by the second light beam.

6. The method of claim 5, wherein detecting imaging light from the random scattering medium includes detecting fluorescence produced by the random scattering medium.

7. The method of claim 1, wherein detecting measurement light from the random scattering medium includes detecting fluorescence produced by the random scattering medium during scanning.

8. The method of claim 1, further comprising, prior to directing the interference beam onto the random scattering medium, calibrating a scanning optical system that performs scanning of the first light beam relative to a wavefront correction system that applies the spatial phase compensation profile to the second light beam.

9. The method of claim 1, wherein scanning the first light beam transversely to the first optic axis includes scanning the first light beam across a first transverse direction and across a second transverse direction.

10. The method of claim 1, wherein generating the first light beam and generating the second light beam comprises generating the first light beam and the second light beam from a laser by diffracting the laser output into at least two beams that are shifted in frequency relative to each other.

11. The method of claim 1, further comprising:
generating the first light beam traveling along the first optic axis and operating at a first frequency; and
generating the second light beam traveling along the second optic axis and operating at a second frequency that is distinct from the first frequency by the difference frequency.

12. An apparatus comprising:
a transverse scanning optical system in a path of a first light beam traveling along a first optic axis, the transverse scanning optical system including a first set of optical elements configured to scan the first light beam along a first direction (X) transverse to the first optic axis and a second set of optical elements configured to scan along a second direction (Y) transverse to the first optic axis;
a wavefront correction system in the path of a second light beam traveling along a second optic axis, the wavefront correction system including a wavefront correction device having a spatial phase profile on its surface;
a beam combiner that receives the first light beam and the second light beam and outputs an interference beam having a beat frequency equal to a difference frequency, which is a difference in frequency between the first light beam and second light beam;
a detection system placed relative to a random scattering medium, which is in the path of the interference beam, the detection system configured to detect measurement light produced by the random scattering medium while the interference beam strikes the random scattering medium and to detect imaging light produced by the random scattering medium while only the second light beam strikes the random scattering medium; and
a control system connected to the transverse scanning optical system, the wavefront correction system, and the detection system.

13. The apparatus of claim 12, further comprising a light source outputting the first light beam operating at a first frequency and outputting the second light beam operating at a second frequency that is distinct from the first frequency by the difference frequency.

14. The apparatus of claim 12, wherein the control system is configured to:
send a signal to the transverse scanning optical system to scan the first light beam transversely to the first optic axis to visit a set of N distinct modes in a spatial frequency domain;
receive a signal from the detection system during scanning;
analyze the difference frequency signal of the received signal at each of the N distinct modes to determine phase and amplitude information in the spatial frequency domain of the detected measurement light;
transform the phase and amplitude information from the spatial frequency domain into a spatial domain; and
output a signal to the wavefront correction device indicating values of the information in the spatial domain.

15. The apparatus of claim 12, further comprising a beam block moveable between a blocking position that is in a path of the first light beam and a non-blocking position that is not in the path of the first light beam.

16. The apparatus of claim 12, wherein the transverse scanning optical system includes an X actuator coupled to the first set of optical elements and a Y actuator coupled to the second set of optical elements, wherein the control system is connected to the X and Y actuators of the transverse scanning optical system.

17. The apparatus of claim 16, wherein the first set of optical elements includes a moveable mirror and the X actuator includes a mirror galvanometer and the second set of optical elements includes a moveable mirror and the Y actuator includes a mirror galvanometer.

18. The apparatus of claim 12, wherein the first set of optical elements includes a moveable mirror and the second set of optical elements includes a moveable mirror, and the wavefront correction device includes a spatial light modulator.

19. The apparatus of claim 12, wherein the detection system is configured to detect fluorescence produced by the random scattering medium while the interference beam strikes the random scattering medium and while only the second light beam strikes the random scattering medium.

20. The apparatus of claim 12, wherein the detection system is configured to detect backscattering from the random scattering medium while the interference beam strikes the random scattering medium and while only the second light beam strikes the random scattering medium.

* * * * *